(12) United States Patent
Kell et al.

(10) Patent No.: US 9,016,159 B2
(45) Date of Patent: Apr. 28, 2015

(54) FLEXIBLE TOOL

(75) Inventors: James Kell, Nottingham (GB);
Samantha H Davies, Derby (GB); Ian J McGill, Helensburgh (GB); Graeme E Rigg, Derby (GB); Mark H Raffles, Nottingham (GB); Mark J Daine, Nottingham (GB); Ming C Kong, Nottingham (GB); Dragos Axinte, Nottingham (GB); Iulian Marinescu, Nottingham (GB); Christopher R J Herbert, Nottingham (GB)

(73) Assignee: Rolls-Royce PLC, London (GB)

( * ) Notice: Subject to any disclaimer, the term of this patent is extended or adjusted under 35 U.S.C. 154(b) by 239 days.

(21) Appl. No.: 13/224,783

(22) Filed: Sep. 2, 2011

(65) Prior Publication Data
US 2012/0067158 A1    Mar. 22, 2012

(30) Foreign Application Priority Data

Sep. 17, 2010   (GB) .................................. 1015566.1

(51) Int. Cl.
*B25J 18/06*    (2006.01)
*A61B 1/00*    (2006.01)
*G02B 23/24*    (2006.01)

(52) U.S. Cl.
CPC ............ *B25J 18/06* (2013.01); *Y10T 74/20323* (2015.01); *A61B 1/00078* (2013.01); *G02B 23/2476* (2013.01)

(58) Field of Classification Search
CPC .................................................. A61B 1/00078
USPC ......... 74/490.01, 490.04, 490.05; 901/14, 15, 901/16, 20, 21, 27, 28; 600/143
See application file for complete search history.

(56) References Cited

U.S. PATENT DOCUMENTS

| | | | | |
|---|---|---|---|---|
| 4,784,042 A | * | 11/1988 | Paynter | 91/534 |
| 5,899,425 A | * | 5/1999 | Corey Jr. et al. | 248/276.1 |
| 7,955,042 B2 | * | 6/2011 | Sugahara et al. | 414/729 |
| 8,224,485 B2 | * | 7/2012 | Unsworth | 700/245 |
| 8,323,297 B2 | * | 12/2012 | Hinman et al. | 606/108 |
| 2005/0099254 A1 | * | 5/2005 | Ohnstein et al. | 335/220 |
| 2006/0258912 A1 | * | 11/2006 | Belson et al. | 600/152 |
| 2008/0021166 A1 | * | 1/2008 | Tong et al. | 525/241 |
| 2008/0045795 A1 | * | 2/2008 | Landry | 600/146 |
| 2008/0205980 A1 | | 8/2008 | Zubiate et al. | |
| 2008/0302200 A1 | * | 12/2008 | Tobey | 74/490.02 |
| 2010/0030377 A1 | * | 2/2010 | Unsworth | 700/245 |

FOREIGN PATENT DOCUMENTS

| | | |
|---|---|---|
| KR | 10-2010-0044405 | 4/2010 |
| WO | WO 2006/060775 A2 | 6/2006 |

(Continued)

OTHER PUBLICATIONS

European Search Report issued in European Application No. 11179839 on Jan. 17, 2012.

(Continued)

*Primary Examiner* — William Kelleher
*Assistant Examiner* — Terence Boes
(74) *Attorney, Agent, or Firm* — Oliff PLC

(57) ABSTRACT

A flexible tool comprises stiffening means switchable in use from a first state of relatively low stiffness to a second state of relatively high stiffness, and subsequently switchable from the second state back to the first state.

14 Claims, 3 Drawing Sheets

(56) References Cited

FOREIGN PATENT DOCUMENTS

| WO | WO 2007/015981 | 2/2007 |
| WO | WO 2007/135577 | 11/2007 |

OTHER PUBLICATIONS

Search Report dated Feb. 7, 2011 issued in British Patent Application No. 1015566.1.

* cited by examiner

FLEXIBLE TOOL

This invention relates to flexible tools of the sort sometimes referred to as "snake-arm robots".

Snake-arm robots are commonly used to perform inspections and other operations in hazardous or confined spaces, particularly where the nature of the space or the presence of obstructions means that there is no line-of-sight access to the region of interest within the space. Such confined spaces exist in many different industrial environments, across a wide range of technologies, for example in nuclear engineering, aircraft, engines, industrial plants, shipbuilding, buildings, roads and pipelines.

Gas turbine engines are used for a number of purposes, including as propulsion engines for ships and aircraft, to power pumps for gas or oil, and for power generation.

When such engines are used on aircraft, they need periodic inspection, maintenance and repair. It is possible to do this by removing the engine from the aircraft and dismantling it, but there are serious disadvantages in this approach. Gas turbine engines are complex machines and their dismantling (and subsequent reassembly) is time-consuming and expensive. In addition, to remove the engine from the aircraft is itself a time-consuming and expensive procedure. While the engine is removed, the aircraft cannot be used, which causes inconvenience and financial loss to the operator. It has therefore become more common in recent years to perform inspections, and where possible other operations, with the engine still installed.

Engines are commonly provided with a number of ports in their outer casings, through which inspection tools can be inserted. These tools allow components within the engine to be inspected. In some cases, inspection tools can also be manoeuvred through the front or rear of the engine, between the blades and vanes. A very limited number of maintenance and repair operations can also be carried out by introducing specially adapted tools through the borescope ports. Among the operations that are commonly carried out this way are borescope inspection, penetrant inspection and ultrasonic inspection.

Because of the great advantages offered by in-situ inspection and repair techniques, it would be desirable to be able to carry out a wider range of operations using such tools. However, the scope of such operations is limited by the dimensions of the borescope port (typically less than 12 mm in diameter) and by the size of subsequent openings inside the engine (e.g. between vanes). It can also be difficult, if not impossible, to access the components furthest from the port because of the tortuous routes and relatively long distances involved.

Flexible borescopes are known, which are similar in principle to medical endoscopes, and these can be useful to reach less accessible places within the engine. However, they can be floppy and difficult to position accurately because of their reduced stiffness. Generally, such devices require mechanical guides to direct them along a predetermined path.

The flexibility of conventional robotic arms is provided by a small number of discrete "elbows", at which rotational joints are provided. This limits their flexibility, and restricts their usefulness in confined spaces. Snake-arm robots (also sometimes referred to as continuum robots, elephant's trunks, octopus arms, tentacles or drivable endoscopes) comprise a large number of segments linked by rotatable joints, and they are therefore more flexible than conventional robotic arms. Control wires within the snake-arm robot are selectively joined to the segments to allow independent control or steering of the separate segments. An operator will typically "drive" the tip of the snake-arm robot through a desired path in the confined space, and software will ensure that the rest of the robot follows and does not foul on any obstructions within the space. It is also possible to control the flexing of such a robot joint-by-joint, or by reference to a Cartesian or other fixed coordinate system.

Although snake-arm robots are known that are small enough to fit through gas turbine borescope ports, their load-carrying capacity is so small (typically of the order of a few grams for a robot 600 mm long) that they are of no use for repair operations. Known snake-arm robots with greater load-carrying capacity have correspondingly greater diameters, and so can not fit through the borescope ports. Furthermore, the longer a snake-arm robot is, the lower its load-carrying capacity at the tip. Known snake-arm robots are therefore of no use to carry out such in-situ operations.

The inventors have devised a snake-arm robot with a significantly improved load-carrying capability, which will permit a much greater range of inspection and repair operations to be carried out on installed engines. Snake-arm robots according to the invention can also be made longer than known robots, for a given load-carrying capacity.

The invention provides a flexible tool and a method of performing an operation using a flexible tool as set out in the claims.

Embodiments of the invention will now be described, by way of example, so that the way in which the invention is to be put into effect may be better understood. Reference will be made to the accompanying drawings, in which.

Figure 1:
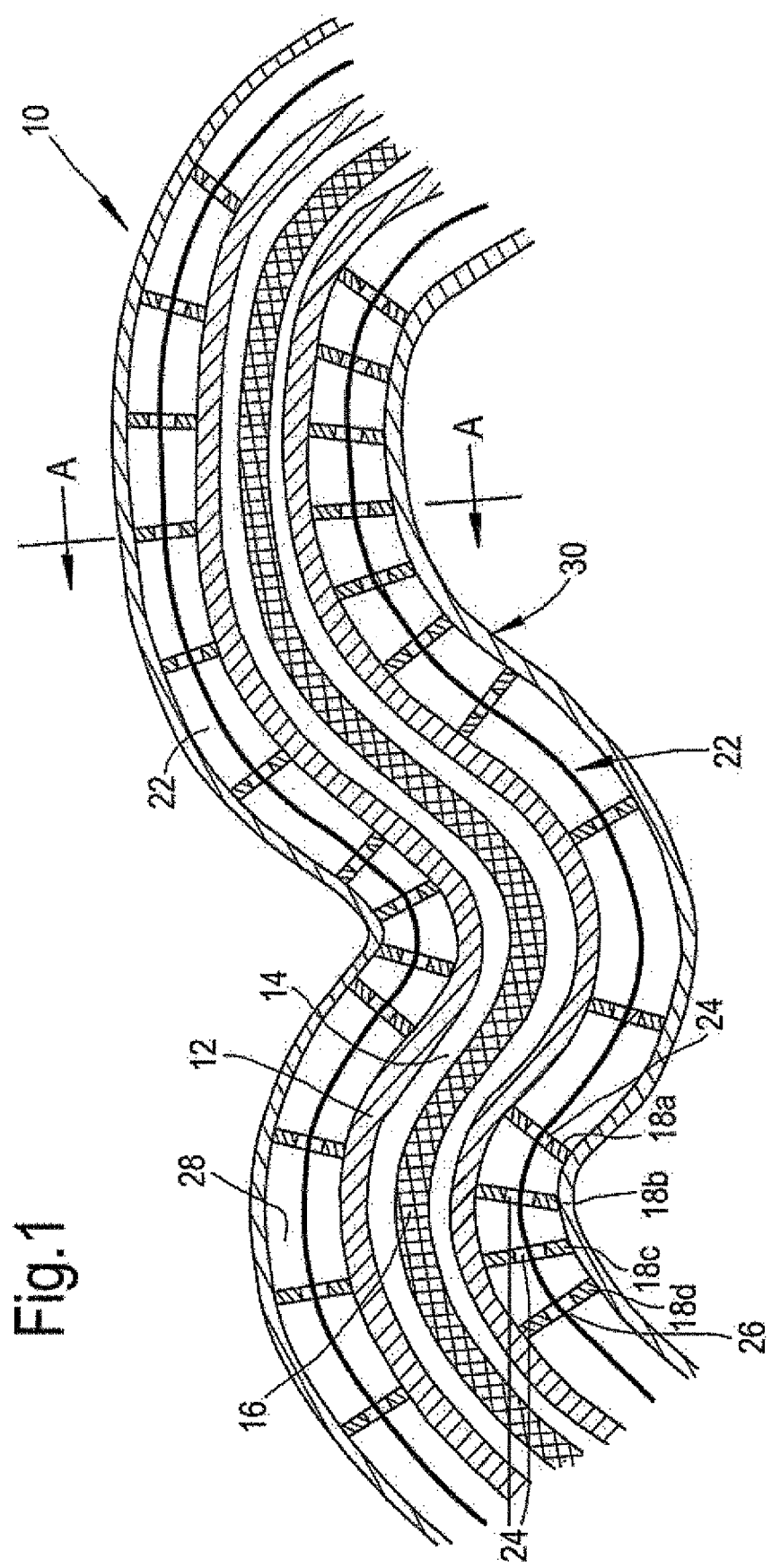
FIG. 1 shows a longitudinal cross-section of part of a flexible tool according to a first embodiment of the invention.
Figure 2:
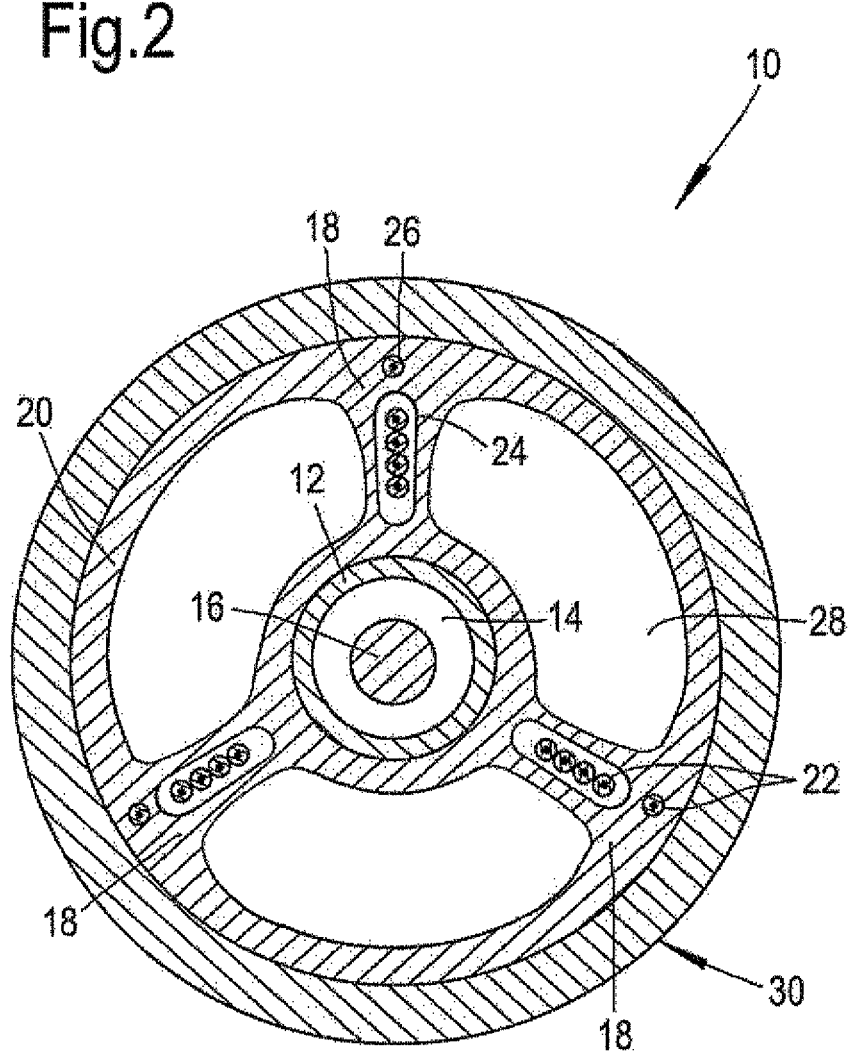
FIG. 2 shows a transverse cross-section on the line A-A shown in FIG. 1.

Referring first to FIGS. 1 and 2, a flexible tool according to the invention, shown generally at 10, has a backbone 12 formed of a flexible material such as a high-temperature-resistant silicone rubber. The backbone 12 is tubular, and defines a central conduit 14. In use, this conduit may accommodate an optical fibre bundle, tool drive cable or the like 16. Spaced along the backbone 12 are radially extending projections 18 supporting a plurality of longitudinally spaced circular ribs 20. In this embodiment, the radially extending projections 18 at each axial position are equally spaced around the circumference of the backbone. It is envisaged that the diameter of the tool is less than 12 mm, so that it can fit through the borescope ports of a gas turbine engine.

The bending of the tool may be controlled in a known manner, as follows. A plurality of sheathed control wires 22 run along the length of the tool (only two are shown in FIG. 1), and through holes 24, 26 in the ribs 18. The wires are free to move through the holes 24 and are guided by them, in contrast to the holes 26 in which the wires are fixed in place. In the embodiment shown, joints in the tool are effectively defined by groups of four projections. The first projection fixes the control wire from the previous joint in a hole 26, while control wires for this and subsequent joints pass through a hole 24. The next two ribs support and guide the control wires through holes 24, and the control wire for this joint is fixed in a hole 26 in the fourth rib of the group.

Considering the four projections indicated in FIG. 1 as 18*a*, 18*b*, 18*c*, 18*d*, the wire 22 is fixed in hole 26 in projection 18*d*, but free to move through holes 24 in projections 18*a*, 18*b* and 18*c*. Therefore, by pulling on the wire 22, the projections 18*a*, 18*b*, 18*c*, 18*d* are pulled closer together, causing a part of the backbone 12 to bend as shown. By suitable control of the plurality of wires 22 any group of four projections 18 can be similarly controlled, and therefore (because the projections 18 extend in different radial directions from the backbone 12) any part of the backbone can be caused to bend in a desired direction. In this way, generally under computer control, the tip of the tool can be steered through obstructions in a workspace to reach the region of interest, and the following parts of the tool can be steered as necessary to follow the tip without fouling the obstructions.

This control mechanism allows the tip of the flexible tool 10 to be steered to any desired position within a workspace, and to avoid obstacles. In use, the tip of the flexible tool would accommodate suitable tools to perform the desired inspection or operation. Such tools may include an optical probe, a light source or a machining tip (driven by a flexible drive shaft carried through the central conduit of the flexible tool).

However, as indicated above, if known snake-arm robots are made small enough to fit through the access spaces of a gas turbine engine then their load-carrying capacity will be inadequate to perform the desired operations; load-carrying capacity is relevant both in terms of the ability to support the weight of the tools and to resist forces generated during, for example, a grinding operation. Conversely, if their load-carrying capacity is increased then they will inevitably become too large to fit through the available access spaces. The invention provides a flexible tool small enough to fit into the limited spaces in a gas turbine engine, but with sufficient load-carrying capacity to enable a wider range of operations to be performed.

Figure 3:
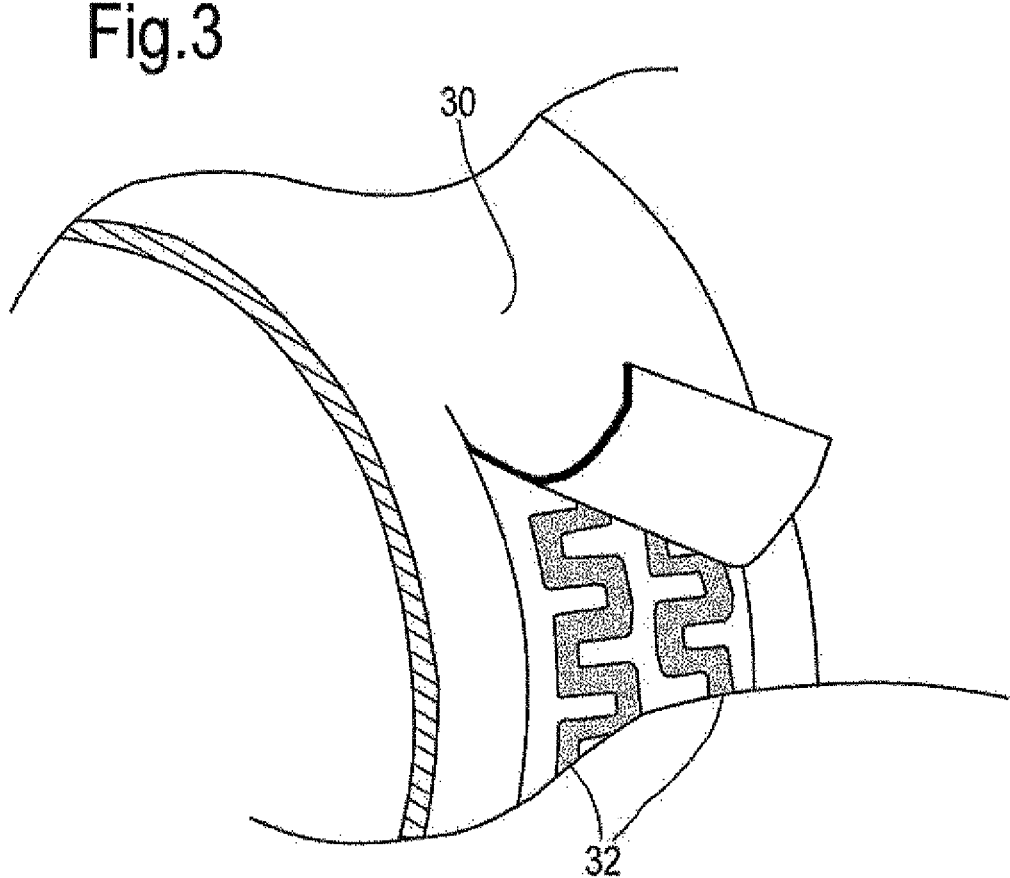
FIG. 3 shows part of the outer surface of the flexible tool of FIG. 1, with the covering layer partly removed.

Referring again to FIGS. 1 and 2, in a flexible tool according to the invention the spaces between the projections 18 and ribs 20 are filled with a cavity-filling medium 28. In the illustrated embodiment, the medium 28 is a thermoplastic which is rigid at the normal operating temperature of the tool. Around the outside of the tool 10, enclosing the ribs 20 and medium 28, is an outer covering or skin 30, which incorporates embedded heating elements. In FIG. 3, part of the skin 30 has been peeled back to show two heating elements 32.

In use, the heating elements 32 are controlled to heat the medium 28 above its glass transition temperature, so that it will melt or soften. In this first state, the medium 28 will not impede the movement of the tool 10 and so the tool may be bent (as described above) to permit the tip to be driven through a workspace to a region of interest. The medium will flow as necessary through the spaces between the projections 18 and ribs 20. A control mechanism may be provided so that, when the medium 28 is in its first state and therefore behaving effectively as a fluid, its pressure may be increased or reduced to control more precisely the stiffness of the flexible tool. In general, a higher fluid pressure will make the tool stiffer, and a lower fluid pressure will make it less stiff. This more precise control may aid the deployment of the tool within the workspace.

Once the tip of the tool is in the desired position, the heating elements are switched off so that the medium 28 will cool. Once the medium 28 cools below its glass transition temperature it will become relatively rigid, and in this second state will effectively lock the ribs 20 and projections 18 in their positions. The entire tool effectively becomes rigid. In this way, the tool 10 is provided with significantly greater rigidity and therefore load-carrying capacity than similar known tools. It is envisaged that, for a tool with a diameter of less than 12 mm, load-carrying capacities will be achievable in the order of 0.2 kg at an overhang distance of 100 mm.

Once the inspection or repair operation is complete, the heating elements 32 are again controlled to heat the medium 28 until it melts or softens back into the first state, after which the tool 10 can be withdrawn from the workspace.

In this way, a tool 10 according to the invention can be made small and (in its first state) flexible enough to fit into confined spaces and through small access ports, such as those in gas turbine engines, but at the same time can be made (by switching into its second state) sufficiently rigid to support appreciable loads, thereby enabling a much wider range of inspection and repair operations to be performed, for example without removing a gas turbine engine from the aircraft wing.

A further advantage may be gained if separate heating elements are provided, spaced along the length of the tool 10. If these heating elements are separately controlled, then it is possible to control the stiffness of the tool segment-by-segment, or joint-by-joint, along its length. This may facilitate the steering of the tool through difficult areas of a workspace. Alternatively, it may allow parts of the tool to be made rigid to allow operations to be performed, while keeping other parts of the tool flexible; for example, to accommodate the movement of other components.

In alternative embodiments of the invention, a different material may be used for the medium 28. For example, it may be a fibre-reinforced thermoplastic, or any other suitable material that can be made more or less stiff by heating and cooling, for example a low-melting-point alloy. It will be understood that the comments above (for example, concerning segment-by-segment control of the tool) would apply equally to such embodiments, with the necessary changes being made to the switching mechanism.

In the embodiments described above, the stiffening and softening of the medium 28 is a repeatable process. In a further alternative embodiment, the medium is a UV-cured adhesive, and the tool is provided with optical fibres or similar light-transmitting elements to carry UV light to the medium when required. In its initial state, the adhesive is soft and so the tool is flexible; once the tool is in the desired position, UV light from a suitable source is directed into the medium to cure it, rendering it stiff and locking the tool in position. After the operations are completed, heat is applied to the adhesive (by embedded heating elements as in the first embodiment described above, or by other means) until the adhesive is degraded sufficiently to lose its stiffness. The tool can then be withdrawn from the workspace. In such an embodiment, the adhesive would not be re-usable; however, it may be possible to remove the degraded adhesive and replace it with new adhesive for the next use of the tool.

In alternative embodiments of the invention, the control of the joints may be achieved by other means than by the control wires described above. For example, hydraulic or pneumatic actuators may be provided, or elements of shape-memory alloy may be provided in the joints which would change their shape or dimensions when subjected to an electrical impulse. It will be understood that such alternative actuators could also be individually controlled.

In another alternative embodiment, not illustrated in the drawings, instead of a single flexible backbone 12 a segmented backbone is provided, with rotatable spherical-type joints between the segments. In this embodiment, the medium acts when stiffened to lock the joints in position, thereby providing rigidity to the tool.

Figure 4:
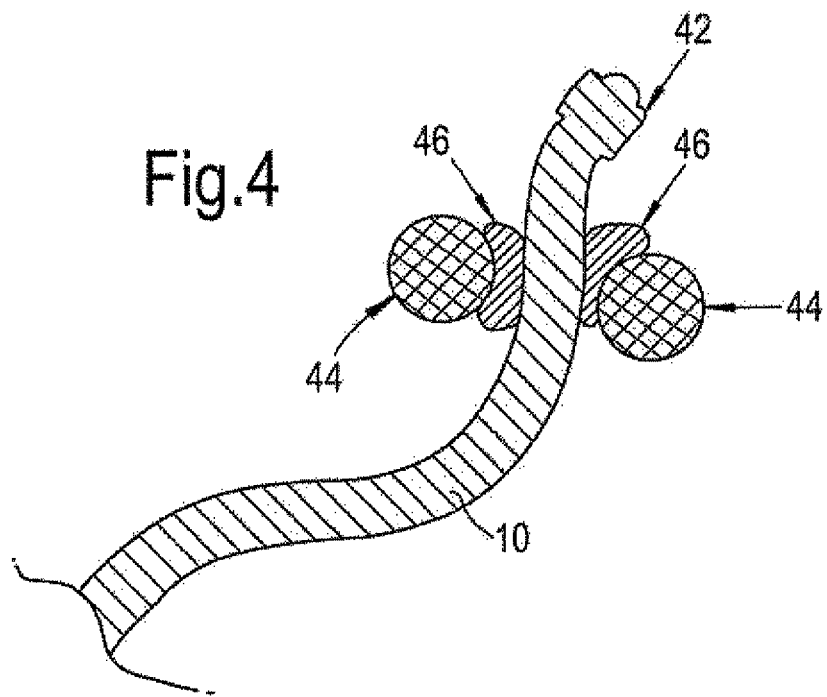
FIG. 4 shows a schematic illustration of a flexible tool according to a second embodiment of the invention.

FIG. 4 illustrates a further, optional feature of a tool according to the invention, which may be combined with any of the embodiments described so far.

In FIG. 4, a tool 10 according to the invention is shown within a workspace. The tip 42 of the tool has been steered between two obstructions 44. In a gas turbine engine, such obstructions may take the form of blades or vanes.

Two inflatable gripping segments 46 are provided towards the tip of the tool, one on each side of the tool. The segments may be formed integrally with the skin of the tool, or may be formed separately and stitched or otherwise attached to the skin.

When the tip of the tool is in the desired position the gripping segments 46 are inflated, as shown in FIG. 4, to support the tool between the obstructions 44. This provides a support for the tool relatively close to its tip, thereby increasing the effective stiffness of the tool. It means that the stiffness of the tool in use is not dependent on the overall length of the tool, but only on the "overhang" between the support and the tip. This enables longer flexible tools to be constructed, to reach more inaccessible workspaces, without sacrificing the rigidity of the tool or its load-carrying capacity.

When the operations have been completed, the gripping segments are deflated so that the tool can be removed.

Other configurations of gripping segments may be used, depending on the particular requirements of the application. For example, a single annular gripping segment or a number of segments spaced around the circumference of the tool. Gripping segments may be provided in multiple positions along the length of the tool, as required.

The gripping segments may also be used for different purposes, enhancing the capabilities of the flexible tool. For example, if the inflatable segments are inflated to secure the tool between two rotatable blades of a gas turbine engine, manual rotation of the engine could then be used to "pull" the tip of the flexible tool to a different position, further around the rotational axis of the engine. In this way, the flexible tool may provide access to regions even further inside the engine and even more remote from the access ports.

It will be appreciated that alternative designs of gripping segments could be used, which would provide the same advantages as the inflatable segments described above. For example, one or more mechanically- or electrically-actuated gripping segments could be used, which would be folded away within the body of the tool to permit its insertion or removal, and deployed outwards from the body to provide support when required.

The invention may also be applied in a simpler flexible tool, in which the control mechanism for the flexing of the tool is absent or is provided only along part of the length of the tool, for example in the region near to the tip. The cavity-filling medium and its associated softening/stiffening mechanism would still be present. Such a tool would be cheaper and simpler to manufacture, and would still provide the advantages of stiffness and load-carrying capacity associated with the embodiments described in more detail above.

Elements of the invention, namely the cavity-filling medium and the gripping segments, may be applied to other designs of snake-arm robots and the like, as well as to those designs specifically described in this specification.

The invention provides a flexible tool to facilitate access to confined or hazardous spaces, but with a greatly enhanced load-carrying capacity compared with known snake-arm robots. The additional load-carrying capacity permits operations such as grinding or deburring to be performed, which have previously been impossible because the tip of the tool has not had sufficient rigidity to react the loads involved.

The invention claimed is:

1. A flexible tool, comprising:
   a cylindrical backbone having a longitudinal axis;
   a plurality of circular ribs encircling the cylindrical backbone, the circular ribs being spaced alone the longitudinal axis of the cylindrical backbone;
   a plurality of projections extending radially outward from the cylindrical backbone, each of the circular ribs being connected with the cylindrical backbone by a portion of the plurality of the projections, the projections of the portion being spaced apart about the periphery of the cylindrical backbone, the circular ribs and the portions of the plurality of the projectings defining plurality of linked segments movable relative to one another; and
   stiffening means comprising a medium that fills spaces between the projections and the circular ribs of the linked segments, wherein
   the medium is switchable in use from a first state of relatively low stiffness in which the medium is fluid to a second state of relatively high stiffness in which the medium is rigid and subsequently switchable from the second state back to the first state, and
   the medium acts in the first state to flow through the spaces to allow relative movement between the linked segments, and the medium acts in the second state to lock the projections and the circular ribs between the linked segments and prevent the relative movement.

2. The flexible tool of claim 1, in which the medium of the stiffening means comprises thermoplastic or fibre-reinforced thermoplastic or low-melting-point alloy or ultraviolet-curable adhesive.

3. The flexible tool of claim 1, wherein the stiffening means is repeatably switchable between the first and second states.

4. The flexible tool of claim 1, wherein switching between the first state and the second state is achieved by selective application of heat to the stiffening means.

5. The flexible tool of claim 1, wherein switching from the first state to the second state is achieved by selective application of ultraviolet light to the stiffening means.

6. The flexible tool of claim 1, further comprising a remotely operated control means to direct flexing of the flexible tool.

7. The flexible tool claim 6, wherein the control means comprises wires or hydraulic or pneumatic actuators or shape-memory alloy elements.

8. The flexible tool of claim 7, wherein the wires are positioned in the medium and extend along the length of the flexible tool.

9. The flexible tool of claim 7, further comprising a plurality of parts or segments that can be flexed independently.

10. The flexible tool of claim 1, further comprising a conduit extending longitudinally through the flexible tool.

11. The flexible tool of claim 1, further comprising a gripping segment actuatable to locate or secure the flexible tool in use.

12. The flexible tool of claim 11, wherein the gripping segment is inflatable.

13. The flexible tool of claim 1, wherein the plurality of projections define holes, the flexible tool further comprising a plurality of wires positioned in the medium and extending through the holes and along the length of the flexible tool, wherein the wires are moveable relative to the plurality of projections and through the holes to bend the flexible tool.

14. A method of performing an operation using the flexible tool of claim 1, the method comprising:
   inserting the flexible tool into a workspace;
   positioning a tip of the flexible tool at a desired position in the workspace;
   switching the stiffening means to the second state;
   performing the operation;
   switching the stiffening means to the first state; and
   removing the flexible tool from the workspace.

* * * * *